United States Patent
Abe et al.

(10) Patent No.: US 6,303,559 B1
(45) Date of Patent: Oct. 16, 2001

(54) DETERGENT COMPOSITION

(75) Inventors: Koji Abe; Reiji Miyahara; Tomiyuki Nanba; Takahiro Akutsu; Toshio Fukuda, all of Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/412,747

(22) Filed: Oct. 5, 1999

(30) Foreign Application Priority Data

Oct. 7, 1998 (JP) .................................................. 10-285269
Oct. 7, 1998 (JP) .................................................. 10-285270
Oct. 7, 1998 (JP) .................................................. 10-285271

(51) Int. Cl.$^7$ ................................ C11D 1/18; C11D 1/10
(52) U.S. Cl. ........................ 510/424; 510/499; 510/119; 510/123
(58) Field of Search .................................. 510/424, 499, 510/119, 123

(56) References Cited

FOREIGN PATENT DOCUMENTS

| 2212598 | 8/1990 | (JP) . |
| 3169846 | 7/1991 | (JP) . |

OTHER PUBLICATIONS

Database WPI, week 199410 & JP 06 033094 A (Kanebo Ltd.).
Database WPI, week 198934 & JP 01 178596 A (Shiseido Co., Ltd.).
Database WPI, week 199638 & JP 08 1839993 A (Shiseido Co., Ltd.).
Database WPI, week 199808 & JP 09 316486 A (Shiseido Co., Ltd.).
Database WPI, week 199343 & JP 05 246829 A (Nippon Oils & Fats Co., Ltd.).
Database WPI, week 199351 & JP 05 311193 A (Nippon Oils & Fats Co., Ltd.
Database WPI, week 199429 & JP 06 172785A (Nippon Oils & Fats Co., Ltd.).
1984 Petter, Fatty acid sulphoalkyl amides and esters as cosmetic surfactants, Int'l Journal of Cosmetic Science. vol. 6, pp. 249–260.*

* cited by examiner

Primary Examiner—Yogendra N. Gupta
Assistant Examiner—Charles Boyer
(74) Attorney, Agent, or Firm—Townsend & Banta

(57) ABSTRACT

The present invention is a detergent composition which characteristically contains 1) an alkali metal N-methyltaurate salt or an organic alkali N-methyltaurate salt of N-acylmethyltaurine, N-acyltaurine, alkylsulfuric ester, alkyl ether sulfuric ester, or alkylsulfonic acid; 2) an alkali metal hypotaurate salt or an organic alkali hypotaurate salt of N-acylmethyltaurine, N-acyltaurine, alkylsulfuric ester, alkyl ether sulfuric ester, or alkylsulfonic acid; or 3) an alkali metal taurate salt or an organic alkali taurate salt of N-acylmethyltaurine, N-acyltaurine, alkylsulfuric ester, alkyl ether sulfuric ester, or alkylsulfonic acid.

4 Claims, No Drawings

DETERGENT COMPOSITION

RELATED APPLICATION

This application claims the priority of Japanese Patent application No. 10-285269 filed on Oct. 7, 1998, No. 10-285270 filed on Oct. 7, 1998, and No. 10-285271 filed on Oct. 7, 1998, which are incorporated herein by reference.

BACKGROUND OF THE INVENTION

1. Field of the Invention

The present invention relates in general to a detergent composition, and more particularly to a detergent composition which foams well and does not leave a slimy feeling after use.

2. The Prior Art

Conventionally, alkyl sulfates have been used as detergents in products such as cleansing foam, body shampoo and shampoo because of their foaming quality and usability. Particularly, since hair washed with alkyl sulfates do not have a squeaky feeling, they have been used as the base agents of shampoos for a long time. They are also used in cleansing foam and body shampoo, not as the main base agent but as an assistant agent to increase foaming because they cause a slimy feeling during use. The range of applications for alkyl sulfates will extend even more if a refreshing feeling can be added to it.

BRIEF SUMMARY OF THE INVENTION

As described above, since alkyl sulfates have the superior characteristic of good foaming, if a refreshing feeling is added to them, they can be used as the main base agent for detergents other than shampoos to obtain detergents with good foaming.

The object of the present invention is to provide a detergent composition which has good foaming and does not leave a slimy feeling after use.

1. Invention Described in claims 1–10

That is, the present invention provides a detergent composition which contains as an essential ingredient an alkali metal N-methyltaurate salt of a N-acylmethyltaurine represented by the following general formula 1-(1).

$$R\text{—}CO\text{—}N(CH_3)\text{—}CH_2\text{—}CH_2\text{—}SO_3^-H_2N^+(CH_3)\text{—}CH_2\text{—}CH_2\text{—}SO_3^-X^+ \quad 1\text{-}(1)$$

(In this formula, R denotes a saturated or unsaturated hydrocarbon group with a carbon number of 7–23 and X denotes an alkali metal.)

Also, the present invention provides a detergent composition which contains as an essential ingredient an organic alkali N-methyltaurate salt of a N-acylmethyltaurine represented by the following general formula 1-(2).

$$R\text{—}CO\text{—}N(CH_3)\text{—}CH_2\text{—}CH_2\text{—}SO_3^-H_2N^+(CH_3)\text{—}CH_2\text{—}CH_2\text{—}SO_3^-Y^+ \quad 1\text{-}(2)$$

(In this formula, R denotes a saturated or unsaturated hydrocarbon group with a carbon number of 7–23 and Y denotes an organic alkali.)

Also, the present invention provides a detergent composition which contains as an essential ingredient an alkali metal N-methyltaurate salt of a N-acyltaurine represented by the following general formula 1-(3).

$$R\text{—}CO\text{—}NH\text{—}CH_2\text{—}CH_2\text{—}SO_3^-H_2N^+(CH_3)\text{—}CH_2\text{—}CH_2\text{—}SO_3^-X^+ \quad 1\text{-}(3)$$

(In this formula, R denotes a saturated or unsaturated hydrocarbon group with a carbon number of 7–23, and X denotes an alkali metal.)

Also, the present invention provides a detergent composition which contains as an essential ingredient an organic alkali N-methyltaurate salt of a N-acyltaurine represented by the following general formula 1-(4).

$$R\text{—}CO\text{—}NH\text{—}CH_2\text{—}CH_2\text{—}SO_3^-H_2N^+(CH_3)\text{—}CH_2\text{—}CH_2\text{—}SO_3^-Y^+ \quad 1\text{-}(4)$$

(In this formula, R denotes a saturated or unsaturated hydrocarbon group with a carbon number of 7–23 and Y denotes an organic alkali.)

Also, the present invention provides a detergent composition which contains as an essential ingredient an alkali metal N-methyltaurate salt of an alkylsulfuric ester represented by the following general formula 1-(5).

$$R\text{—}O\text{—}SO_3^-H_2N^+(CH_3)\text{—}CH_2\text{—}CH_2\text{—}SO_3^-X^+ \quad 1\text{-}(5)$$

(In this formula, R denotes a saturated or unsaturated hydrocarbon group with a carbon number of 7–23 and X denotes an alkali metal.)

Also, the present invention provides a detergent composition which contains as an essential ingredient an organic alkali N-methyltaurate salt of an alkylsulfuric ester represented by the following general formula 1-(6).

$$R\text{—}O\text{—}SO_3^-H_2N^+(CH_3)\text{—}CH_2\text{—}CH_2\text{—}SO_3^-Y^+ \quad 1\text{-}(6)$$

(In this formula, R denotes a saturated or unsaturated hydrocarbon group with a carbon number of 7–23 and Y denotes an organic alkali.)

Also, the present invention provides a detergent composition which contains as an essential ingredient an alkali metal N-methyltaurate salt of an alkyl ether sulfuric ester represented by the following general formula 1-(7).

$$R\text{—}O\text{—}(CH_2CH_2O)_n SO_3^-H_2N^+(CH_3)\text{—}CH_2\text{—}CH_2SO_3^-X^+ \quad 1\text{-}(7)$$

(In this formula, R denotes a saturated or unsaturated hydrocarbon group with a carbon number of 7–23, n denotes an integer 1–40, and X denotes an alkali metal.)

Also, the present invention provides a detergent composition which contains as an essential ingredient an organic alkali N-methyltaurate salt of an alkyl ether sulfuric ester represented by the following general formula 1-(8).

$$R\text{—}O\text{—}(CH_2CH_2O)_n SO_3^-H_2N^+(CH_3)\text{—}CH_2\text{—}CH_2\text{—}SO_3^-Y^+ \quad 1\text{-}(8)$$

(In this formula, R denotes a saturated or unsaturated hydrocarbon group with a carbon number of 7–23, n denotes an integer 1–40, and Y denotes an organic alkali.)

Also, the present invention provides a detergent composition which contains as an essential ingredient an alkali metal N-methyltaurate salt of an alkylsulfonic acid represented by the following general formula 1-(9).

$$R\text{—}SO_3^-H_2N^+(CH_3)\text{—}CH_2\text{—}CH_2\text{—}SO_3^-X^+ \quad 1\text{-}(9)$$

(In this formula, R denotes a saturated or unsaturated hydrocarbon group with a carbon number of 7–23 and X denotes an alkali metal.)

Also, the present invention provides a detergent composition which contains as an essential ingredient an organic alkali N-methyltaurate salt of an alkylsulfonic acid represented by the following general formula 1-(10).

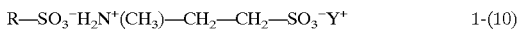  1-(10)

(In this formula, R denotes a saturated or unsaturated hydrocarbon group with a carbon number of 7–23 and Y denotes an organic alkali.)

2. Invention Described in claims 11–20

That is, the present invention provides a detergent composition which contains as an essential ingredient an alkali metal hypotaurate salt of a N-acylmethyltaurine represented by the following general formula 2-(1).

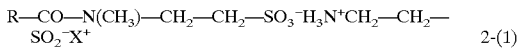  2-(1)

(In this formula, R denotes a saturated or unsaturated hydrocarbon group with a carbon number of 7–23 and X denotes an alkali metal.)

Also, the present invention provides a detergent composition which contains as an essential ingredient an organic alkali hypotaurate salt of a N-acylmethyltaurine represented by the following general formula 2-(2).

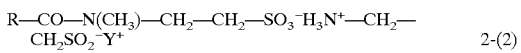  2-(2)

(In this formula, R denotes a saturated or unsaturated hydrocarbon group with a carbon number of 7–23 and Y denotes an organic alkali.)

Also, the present invention provides a detergent composition which contains as an essential ingredient an alkali metal hypotaurate salt of a N-acyltaurine represented by the following general formula 2-(3).

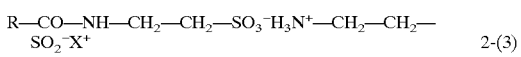  2-(3)

(In this formula, R denotes a saturated or unsaturated hydrocarbon group with a carbon number of 7–23, and X denotes an alkali metal.)

Also, the present invention provides a detergent composition which contains as an essential ingredient an organic alkali hypotaurate salt of a N-acyltaurine represented by the following general formula 2-(4).

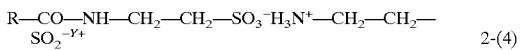  2-(4)

(In this formula, R denotes a saturated or unsaturated hydrocarbon group with a carbon number of 7–23 and Y denotes an organic alkali.)

Also, the present invention provides a detergent composition which contains as an essential ingredient an alkali metal hypotaurate salt of an alkylsulfuric ester represented by the following general formula 2-(5).

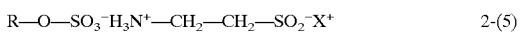  2-(5)

(In this formula, R denotes a saturated or unsaturated hydrocarbon group with a carbon number of 7–23 and X denotes an alkali metal.)

Also, the present invention provides a detergent composition which contains as an essential ingredient an organic alkali hypotaurate salt of an alkylsulfuric ester represented by the following general formula 2-(6)

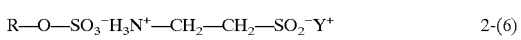  2-(6)

(In this formula, R denotes a saturated or unsaturated hydrocarbon group with a carbon number of 7–23 and Y denotes an organic alkali.)

Also, the present invention provides a detergent composition which contains as an essential ingredient an alkali metal hypotaurate salt of an alkyl ether sulfuric ester represented by the following general formula 2-(7).

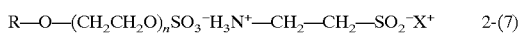  2-(7)

(In this formula, R denotes a saturated or unsaturated hydrocarbon group with a carbon number of 7–23, n denotes an integer 1–40, and X denotes an alkali metal.)

Also, the present invention provides a detergent composition which contains as an essential ingredient an organic alkali hypotaurate salt of an alkyl ether sulfuric ester represented by the following general formula 2-(8).

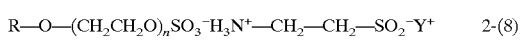  2-(8)

(In this formula, R denotes a saturated or unsaturated hydrocarbon group with a carbon number of 7–23, n denotes an integer 1–40, and Y denotes an organic alkali.)

Also, the present invention provides a detergent composition which contains as an essential ingredient an alkali metal hypotaurate salt of an alkylsulfonic acid represented by the following general formula 2-(9).

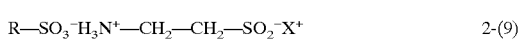  2-(9)

(In this formula, R denotes a saturated or unsaturated hydrocarbon group with a carbon number of 7–23 and X denotes an alkali metal.)

Also, the present invention provides a detergent composition which contains as an essential ingredient an organic alkali hypotaurate salt of an alkylsulfonic acid represented by the following general formula 2-(10).

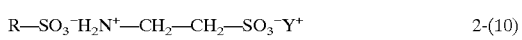  2-(10)

(In this formula, R denotes a saturated or unsaturated hydrocarbon group with a carbon number of 7–23 and Y denotes an organic alkali.)

3. Invention Described in claims 21–30

That is, the present invention provides a detergent composition which contains as an essential ingredient an alkali metal taurate salt of a N-acylmethyltaurine represented by the following general formula 3-(1).

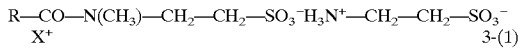  3-(1)

(In this formula, R denotes a saturated or unsaturated hydrocarbon group with a carbon number of 7–23 and X denotes an alkali metal.)

Also, the present invention provides a detergent composition which contains as an essential ingredient an organic alkali taurate salt of a N-acylmethyltaurine represented by the following general formula 3-(2).

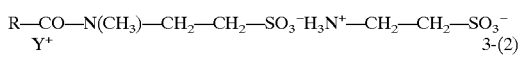  3-(2)

(In this formula, R denotes a saturated or unsaturated hydrocarbon group with a carbon number of 7–23 and Y denotes an organic alkali.)

Also, the present invention provides a detergent composition which contains as an essential ingredient an alkali metal taurate salt of a N-acyltaurine represented by the following general formula 3-(3).

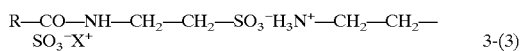

$$R\text{—}CO\text{—}NH\text{—}CH_2\text{—}CH_2\text{—}SO_3^-H_3N^+\text{—}CH_2\text{—}CH_2\text{—}SO_3^-X^+ \quad 3\text{-}(3)$$

(In this formula, R denotes a saturated or unsaturated hydrocarbon group with a carbon number of 7–23, and X denotes an alkali metal.)

Also, the present invention provides a detergent composition which contains as an essential ingredient an organic alkali taurate salt of a N-acyltaurine represented by the following general formula 3-(4).

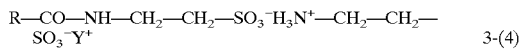

$$R\text{—}CO\text{—}NH\text{—}CH_2\text{—}CH_2\text{—}SO_3^-H_3N^+\text{—}CH_2\text{—}CH_2\text{—}SO_3^-Y^+ \quad 3\text{-}(4)$$

(In this formula, R denotes a saturated or unsaturated hydrocarbon group with a carbon number of 7–23 and Y denotes an organic alkali.)

Also, the present invention provides a detergent composition which contains as an essential ingredient an alkali metal taurate salt of an alkylsulfuric ester represented by the following general formula 3-(5).

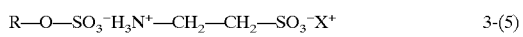

$$R\text{—}O\text{—}SO_3^-H_3N^+\text{—}CH_2\text{—}CH_2\text{—}SO_3^-X^+ \quad 3\text{-}(5)$$

(In this formula, R denotes a saturated or unsaturated hydrocarbon group with a carbon number of 7–23 and X denotes an alkali metal.)

Also, the present invention provides a detergent composition which contains as an essential ingredient an organic alkali taurate salt of an alkylsulfuric ester represented by the following general formula 3-(6).

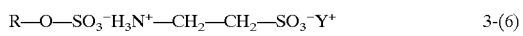

$$R\text{—}O\text{—}SO_3^-H_3N^+\text{—}CH_2\text{—}CH_2\text{—}SO_3^-Y^+ \quad 3\text{-}(6)$$

(In this formula, R denotes a saturated or unsaturated hydrocarbon group with a carbon number of 7–23 and Y denotes an organic alkali.)

Also, the present invention provides a detergent composition which contains as an essential ingredient an alkali metal taurate salt of an alkyl ether sulfuric ester represented by the following general formula 3-(7).

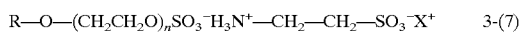

$$R\text{—}O\text{—}(CH_2CH_2O)_n SO_3^-H_3N^+\text{—}CH_2\text{—}CH_2\text{—}SO_3^-X^+ \quad 3\text{-}(7)$$

(In this formula, R denotes a saturated or unsaturated hydrocarbon group with a carbon number of 7–23, n denotes an integer 1–40, and X denotes an alkali metal.)

Also, the present invention provides a detergent composition which contains as an essential ingredient an organic alkali taurate salt of an alkyl ether sulfuric ester represented by the following general formula 3-(8).

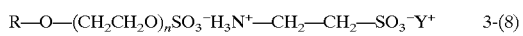

$$R\text{—}O\text{—}(CH_2CH_2O)_n SO_3^-H_3N^+\text{—}CH_2\text{—}CH_2\text{—}SO_3^-Y^+ \quad 3\text{-}(8)$$

(In this formula, R denotes a saturated or unsaturated hydrocarbon group with a carbon number of 7–23, n denotes an integer 1–40, and Y denotes an organic alkali.)

Also, the present invention provides a detergent composition which contains as an essential ingredient an alkali metal taurate salt of an alkylsulfonic acid represented by the following general formula 3-(9).

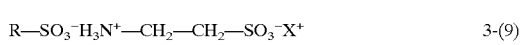

$$R\text{—}SO_3^-H_3N^+\text{—}CH_2\text{—}CH_2\text{—}SO_3^-X^+ \quad 3\text{-}(9)$$

(In this formula, R denotes a saturated or unsaturated hydrocarbon group with a carbon number of 7–23 and X denotes an alkali metal.)

Also, the present invention provides a detergent composition which contains as an essential ingredient an organic alkali taurate salt of an alkylsulfonic acid represented by the following general formula 3-(10).

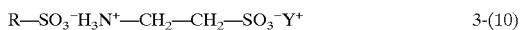

$$R\text{—}SO_3^-H_3N^+\text{—}CH_2\text{—}CH_2\text{—}SO_3^-Y^+ \quad 3\text{-}(10)$$

(In this formula, R denotes a saturated or unsaturated hydrocarbon group with a carbon number of 7–23 and Y denotes an organic alkali.)

DETAILED DESCRIPTION OF THE INVENTION

The present invention is described in detail below.

In the compounds blended, as an essential ingredient, into the detergent composition of the present invention represented by the above general formulas 1-, 2-, and 3-(1)–(10), R denotes a saturated or unsaturated hydrocarbon group with a carbon number of 7–23. Specific examples include linear saturated hydrocarbon groups such as a heptyl group, octyl group, nonyl group, decyl group, undecyl group, dodecyl group, tridecyl group, tetradecyl group, pentadecyl group, hexadecyl group, heptadecyl group, octadecyl group and tetraeicosyl group, branched saturated hydrocarbon groups such as a 2-ethylheptadecyl group and 2-ethylpentyl group, linear unsaturated hydrocarbon groups such as a 8-heptadecenyl group, oleyl group and 4,6-octadecadiethenyl group, and branched unsaturated hydrocarbon groups such as a 2-methyloctadeca-6-ethenyl group.

In the aforementioned general formulas 1-, 2-, and 3-(1), (3), (5), (7), and (9), X denotes an alkali metal such as sodium, potassium or lithium. In the general formulas 1-, 2-, and 3-(2), (4), (6), (8), and (10), Y denotes an organic alkali such as triethanol amine, diethanol amine or lysine.

Specific examples of the compounds blended, as an essential ingredient, into the detergent composition of the present invention represented by the above general formulas 1-(1)–(10); an example is given below for each general formula.

General formula 1-(1): Sodium N-methyltaurate N-lauroylmethyltaurate
General formula 1-(2): Triethanol amine N-methyltaurate N-lauroylmethyltaurate
General formula 1-(3): Sodium N-methyltaurate N-lauroyltaurate
General formula 1-(4): Triethanol amine N-methyltaurate N-lauroyltaurate
General formula 1-(5): Sodium N-methyltaurate laurylsulfuric ester
General formula 1-(6): Triethanol amine N-methyltaurate laurylsulfuric ester
General formula 1-(7): Sodium N-methyltaurate polyoxyethylenelauryl ether sulfuric ester
General formula 1-(8): Triethanol amine N-methyltaurate polyoxyethylenelauryl ether sulfuric ester
General formula 1-(9): Sodium N-methyltaurate laurylsulfonate
General formula 1-(10): Triethanol amine N-methyltaurate laurylsulfonate Specific examples of the compounds blended, as an essential ingredient, into the detergent composition of the present invention represented by the above general formulas 2-(1)–(10); an example is given below for each general formula.

General formula 2-(1): Sodium hypotaurate N-lauroylmethyltaurate

General formula 2-(2): Triethanol amine hypotaurate N-lauroylmethyltaurate
General formula 2-(3): Sodium hypotaurate N-lauroyltaurate
General formula 2-(4): Triethanol amine hypotaurate N-lauroyltaurate
General formula 2-(5): Sodium hypotaurate laurylsulfuric ester
General formula 2-(6): Triethanol amine hypotaurate laurylsulfuric ester
General formula 2-(7): Sodium hypotaurate polyoxyethylenelauryl ether sulfuric ester
General formula 2-(8): Triethanol amine hypotaurate polyoxyethylenelauryl ether sulfuric ester
General formula 2-(9): Sodium hypotaurate laurylsulfonate
General formula 2-(10): Triethanol amine hypotaurate laurylsulfonate Specific examples of the compounds blended, as an essential ingredient, into the detergent composition of the present invention represented by the above general formulas 3-(1)-(10); an example is given below for each general formula.

General formula 3-(1): Sodium taurate N-lauroylmethyltaurate
General formula 3-(2): Triethanol amine taurate N-lauroylmethyltaurate
General formula 3-(3): Sodium taurate N-lauroyltaurate
General formula 3-(4): Triethanol amine taurate N-lauroyltaurate
General formula 3-(5): Sodium taurate laurylsulfuric ester
General formula 3-(6): Triethanol amine taurate laurylsulfuric ester
General formula 3-(7): Sodium taurate polyoxyethylenelauryl ether sulfuric ester
General formula 3-(8): Triethanol amine taurate polyoxyethylenelauryl ether sulfuric ester
General formula 3-(9): Sodium taurate laurylsulfonate
General formula 3-(10): Triethanol amine taurate laurylsulfonate The blend ratio of the compounds blended, as an essential ingredient, into the detergent composition of the present invention represented by the above general formulas 1-, 2-, and 3-(1)–(10) is preferably 0.5–90 wt %. A more preferable blend ratio range is 5–40 wt %; by using a detergent composition prepared within this range, the effect of the present invention can be more clearly obtained. If the blend ratio is 0.5 wt % or less, then the effect of the present invention is hard to obtain. It is not preferable to have a blend ratio of more than 90 wt %, because then problems arise such as a reduction of the solubility in water.

Preparation methods of the compounds blended, for an essential ingredient, into the detergent composition of the present invention represented by the above general formulas 1-(1)–(10) include a method in which N-acylmethyltaurine, N-acyltaurine, alkylsulfuric ester, alkyl ether sulfuric ester, or alkylsulfonic acid is dissolved at a temperature of approximately 80° C. and an aqueous solution of the alkali metal N-methyltaurate salt or the organic alkali N-methyltaurate salt is added to it while being stirred, or an aqueous solution of the N-methyltaurine and an aqueous solution of the other alkali are separately added to it while being stirred.

Preparation methods of the compounds blended, for an essential ingredient, into the detergent composition of the present invention represented by the above general formulas 2-(1)–(10) include a method in which N-acylmethyltaurine, N-acyltaurine, alkylsulfuric ester, alkyl ether sulfuric ester, or alkylsulfonic acid is dissolved at a temperature of approximately 80° C. and an aqueous solution of the alkali metal hypotaurate salt or the organic alkali hypotaurate salt is added to it while being stirred, or an aqueous solution of the hypotaurine and an aqueous solution of the other alkali are separately added to it while being stirred.

Preparation methods of the compounds blended, for an essential ingredient, into the detergent composition of the present invention represented by the above general formulas 3-(1)–(10) include a method in which N-acylmethyltaurine, N-acyltaurine, alkylsulfuric ester, alkyl ether sulfuric ester, or alkylsulfonic acid is dissolved at a temperature of approximately 80° C. and an aqueous solution of the alkali metal taurate salt or the organic alkali taurate salt is added to it while being stirred, or an aqueous solution of the taurine and an aqueous solution of the other alkali are separately added to it while being stirred.

The detergent composition of the present invention refers to a composition which has a cleaning effect on objects. The range of objects to be cleaned is not limited. Preferably, it refers to a detergent used on human bodies, such as cosmetics and quasi-drugs. In addition to the aforementioned essential ingredients, other ingredients which are usually contained in a detergent composition can also be blended in, including anionic surfactants such as soap, a alkylsulfuric ester (salt), polyoxyethylenealkyl ether sulfuric acid (salt) and hydroxyalkyl ether carboxylic acid (salt), ampholytic surfactants such as imidazoline type ampholytic surfactants and betaine type ampholytic surfactants, non-ionic surfactants such as a polyoxyethylene alkyl ether, polyoxyethylene fatty acid ester, sucrose fatty acid ester, alkylglycoside and maltitolhydroxy aliphatic ether, cationic surfactants such as trimethylalkyl ammonium chloride, humectants such as glycerine, 1,3-butylene glycol and dipropylene glycol, extracts of plants such as Swertia japonica, Paeonia lactiflora, Iris florentina and Horsetail (Equisetum), drugs such as tranexamic acid and arbutin, perfumes and preservatives.

EXAMPLES

The present invention is further described in detail below. The present invention is not limited to these examples.
(Testing)
The compounds represented by the aforementioned general formulas 1-, 2-, and 3-(1)–(10) were subjected to a foaming test and an actual use test.
1. Foaming Test with the Shaking Method
0.5 wt % of each sample in Table 1 was dissolved in ion exchanged water with 70 ppm calcium chloride already dissolved in it. The pH was then adjusted to 7.0 with hydrochloric acid. This solution was kept at 30° C. and 20 ml of it was put into a Nessler's tube with an inner diameter of 3 cm and a height of 20 cm equipped with a sliding plug, and then tilted 90 degrees every second using a pendulum shaker. After one minute, the sample was taken out of the shaker and the foam height was measured. The time required for the foam height to be reduced to half of the original height (duration) was also measured.
(Sensory Test of Actual Use)
Fifty panelists were used to conduct the actual use test. 10 ml of a 10% aqueous solution of each sample was put on a hand and the hand was washed for 30 seconds. The feeling during use and after rinsing was rated with a five point scale based on the criteria shown in Table 1. The average of the fifty panelists was calculated to obtain the total evaluation.

TABLE 1

| Evaluation point | Foaming | Sliminess after use |
|---|---|---|
| 5 | Considerably good | Considerably refreshing |
| 4 | Somewhat good | Somewhat refreshing |
| 3 | Average | Average |
| 2 | Somewhat poor | Somewhat slimy |
| 1 | Considerably poor | Considerably slimy |

⊙: The average of the evaluation points is 4–5.

o: The average of the evaluation points is 3–3.9.

Δ: The average of the evaluation points is 2–2.9.

X: The average of the evaluation points is 1–1.9.

1. Examples of claims 1–10

(Test Samples 1 and 2, Control Samples 1–3)

Using the compounds shown in Table 2 (test samples 1 and 2 are, respectively, the compounds represented by the general formulas (1) and (2)), the foaming test and the actual use test were carried out for each sample. The results are shown in Table 3.

TABLE 2

| Sample No. | Compound name |
|---|---|
| Test sample 1 | Sodium N-methyltaurate N-lauroylmethyltaurate |
| Test sample 2 | Triethanol amine N-methyltaurate N-lauroylmethyltaurate |
| Control sample 1 | Sodium N-lauroylmethyltaurate |
| Control sample 2 | Potassium N-lauroylmethyltaurate |
| Control sample 3 | Triethanol amine N-lauroylmethyltaurate |

TABLE 3

| | Results of the foaming test | | Results of the actual use test | |
|---|---|---|---|---|
| | Foam height (cm) | Duration (min) | Foaming | Sliminess after use |
| Test sample 1 | 15.8 | 200 | ⊙ | o |
| Test sample 2 | 16.0 | 150 | ⊙ | ⊙ |
| Control sample 1 | 11.5 | 40 | ⊙ | x |
| Control sample 2 | 12.0 | 50 | o | Δ |
| Control sample 3 | 13.0 | 70 | o | x |

(Test Samples 3 and 4, Control Samples 4–6)

Using the compounds shown in Table 4 (test samples 3 and 4 are, respectively, the compounds represented by the general formulas (3) and (4)), the foaming test and the actual use test were carried out for each sample. The results are shown in Table 5.

TABLE 4

| Sample No. | Compound name |
|---|---|
| Test sample 3 | Sodium N-methyltaurate N-lauroyltaurate |
| Test sample 4 | Triethanol amine N-methyltaurate N-lauroyltaurate |
| Control sample 4 | Sodium N-lauroyltaurate |
| Control sample 5 | Potassium N-lauroyltaurate |
| Control sample 6 | Triethanol amine N-lauroyltaurate |

TABLE 5

| | Results of the foaming test | | Results of the actual use test | |
|---|---|---|---|---|
| | Foam height (cm) | Duration (min) | Foaming | Sliminess after use |
| Test sample 3 | 14.8 | 310 | ⊙ | o |
| Test sample 4 | 13.0 | 280 | ⊙ | o |
| Control sample 4 | 10.5 | 60 | o | x |
| Control sample 5 | 11.5 | 40 | o | Δ |
| Control sample 6 | 11.0 | 75 | o | Δ |

(Test Samples 5 and 6, Control Samples 7–9)

Using the compounds shown in Table 6 (test samples 5 and 6 are, respectively, the compounds represented by the general formulas (5) and (6)), the foaming test and the actual use test were carried out for each sample. The results are shown in Table 7.

TABLE 6

| Sample No. | Compound name |
|---|---|
| Test sample 5 | Sodium N-methyltaurate laurylsulfuric ester |
| Test sample 6 | Triethanol amine N-methyltaurate laurylsulfuric ester |
| Control sample 7 | Sodium lauroylsulfuric ester |
| Control sample 8 | Potassium lauroylsulfuric ester |
| Control sample 9 | Triethanol amine lauroylsulfuric ester |

TABLE 7

| | Results of the foaming test | | Results of the actual use test | |
|---|---|---|---|---|
| | Foam height (cm) | Duration (min) | Foaming | Sliminess after use |
| Test sample 5 | 20.5 | 340 | ⊙ | ⊙ |
| Test sample 6 | 19.0 | 300 | ⊙ | o |
| Control sample 7 | 18.0 | 100 | ⊙ | x |

TABLE 7-continued

| | Results of the foaming test | | Results of the actual use test | |
|---|---|---|---|---|
| | Foam height (cm) | Duration (min) | Foaming | Sliminess after use |
| Control sample 8 | 14.0 | 150 | ⊚ | x |
| Control sample 9 | 13.9 | 90 | ⊚ | x |

(Test Samples 7 and 8, Control Samples 10–12)

Using the compounds shown in Table 8 (test samples 7 and 8 are, respectively, the compounds represented by the general formulas (7) and (8)), the foaming test and the actual use test were carried out for each sample. The results are shown in Table 9.

TABLE 8

| Sample No. | Compound name |
|---|---|
| Test sample 7 | Sodium N-methyltaurate polyoxytethylenelauryl ether sulfuric ester |
| Test sample 8 | Triethanol amine N-methyltaurate polyoxytethylenelauryl ether sulfuric ester |
| Control sample 10 | Sodium polyoxytethylenelauryl ether sulfuric ester |
| Control sample 11 | Potassium polyoxytethylenelauryl ether sulfuric ester |
| Control sample 12 | Triethanol amine polyoxytethylenelauryl ether sulfuric ester |

TABLE 9

| | Results of the foaming test | | Results of the actual use test | |
|---|---|---|---|---|
| | Foam height (cm) | Duration (min) | Foaming | Sliminess after use |
| Test sample 7 | 16.5 | 250 | ⊚ | ⊚ |
| Test sample 8 | 15.0 | 300 | ⊚ | ⊚ |
| Control sample 10 | 10.0 | 80 | ⊚ | x |
| Control sample 11 | 12.0 | 100 | ⊚ | x |
| Control sample 12 | 9.8 | 75 | ○ | x |

(Test Samples 9 and 10, Control Samples 13–15)

Using the compounds shown in Table 10 (test samples 9 and 10 are, respectively, the compounds represented by the general formulas (9) and (10)), the foaming test and the actual use test were carried out for each sample. The results are shown in Table 11.

TABLE 10

| Sample No. | Compound name |
|---|---|
| Test sample 9 | Sodium N-methyltaurate laurylsulfonate |
| Test sample 10 | Triethanol amine N-methyltaurate laurylsulfonate |
| Control sample 13 | Sodium laurylsulfonate |
| Control sample 14 | Potassium laurylsulfonate |
| Control sample 15 | Triethanol amine laurylsulfonate |

TABLE 11

| | Results of the foaming test | | Results of the actual use test | |
|---|---|---|---|---|
| | Foam height (cm) | Duration (min) | Foaming | Sliminess after use |
| Test sample 9 | 22.5 | 470 | ⊚ | ⊚ |
| Test sample 10 | 19.0 | 390 | ⊚ | ○ |
| Control sample 13 | 14.0 | 120 | ⊚ | x |
| Control sample 14 | 13.5 | 95 | ⊚ | x |
| Control sample 15 | 15.8 | 70 | ⊚ | x |

The above results indicate that the test samples, compared with the control samples, have superior foaming and duration of foam and do not give rise to sliminess after use.

Specific examples of the detergent composition pertaining to the present invention are shown below. The blend ratios are expressed in weight percent units.

Example 1

Shampoo

| | wt % |
|---|---|
| (1) Ethylene glycol fatty acid ester | 2.0 |
| (2) Sodium N-methyltaurate N-lauroylmethyltaurate | 10.0 |
| (3) Dodecyl maltoside | 5.0 |
| (4) Laurylsulfobetaine | 10.0 |
| (5) Diethanolamide laurate | 5.0 |
| (6) Propylene glycol | 2.0 |
| (7) Coloring agent, perfume | Appropriate amount |
| (8) Purified water | Balance |

(Preparation method)

Purified water was heated up to 70° C., the other ingredients were added to it and dissolved homogeneously, then it was cooled.

Example 2

Shampoo

| | wt % |
|---|---|
| (1) Sodium cocoylmethyl taurate | 8.0 |
| (2) Triethanolamine N-methyltaurate laurylsulfuric ester | 20.0 |
| (3) Diethanol amide of coconut fatty acid | 4.0 |
| (4) Perfume | Appropriate amount |

-continued

| | wt % |
|---|---|
| (5) EDTA · 2Na | Appropriate amount |
| (6) Purified water | Balance |

(Preparation Method)
Purified water was heated up to 70° C., the other ingredients were added to it and dissolved homogeneously, then it was cooled.

Example 3
Body Shampoo

| | wt % |
|---|---|
| (1) Glycerine | 5.0 |
| (2) Potassium N-methyltaurate polyoxyethylene-lauryl ether sulfuric ester | 5.0 |
| (3) Myristic ester of sucrose | 1.0 |
| (4) Triethanolamine laurate | 10.0 |
| (5) Sodium laurylsulfonsuccinate | 5.0 |
| (6) Diethanol amide of coconut oil | 3.0 |
| (7) Chelating agent | 0.1 |
| (8) Coloring agent, perfume | Appropriate amount |
| (9) Purified water | Balance |

(Preparation Method)
Purified water was heated up to 70° C., the other ingredients were added to it and dissolved homogeneously, then it was cooled.

Example 4
Liquid Soap

| | wt % |
|---|---|
| (1) Lauric acid | 3.0 |
| (2) Myristic acid | 7.0 |
| (3) Palmitic acid | 3.0 |
| (4) Oleic acid | 2.5 |
| (5) Lauroyldiethanolamide | 6.0 |
| (6) Propylene glycol | 11.0 |
| (7) Erythritol | 4.0 |
| (8) Sodium N-methyltaurate N-lauroylmethyltaurate | 10.0 |
| (9) Sucrose | 5.0 |
| (10) Sodium hydroxide | 3.0 |
| (11) EDTA | 0.1 |
| (12) Perfume | Appropriate amount |
| (13) Purified water | Balance |

(Preparation Method)
Purified water was heated up to 70° C., the other ingredients were added to it and dissolved homogeneously, then it was cooled.

Example 5
Liquid Detergent for Clothes

| | wt % |
|---|---|
| (1) Sodium POE (3 moles) lauryl ether sulfate | 10.0 |
| (2) Maltotritol dodecyl ether | 30.0 |

-continued

| | wt % |
|---|---|
| (3) Sodium N-lauroyltaurate | 15.0 |
| (4) Distearyldimethylammonium chloride | 2.0 |
| (5) Bleach | Appropriate amount |
| (6) Purified water | Balance |

(Preparation Method)
Purified water was heated up to 70° C., the other ingredients were added to it and dissolved homogeneously, then it was cooled.

Example 6
Shampoo

| | wt % |
|---|---|
| (1) Sodium N-methyltaurate N-lauroylmethyltaurate | 10.0 |
| (2) Sodium cocoyl amide propyldimethyl glycine | 5.0 |
| (3) Coconut fatty acid monoethanol amide | 2.0 |
| (4) Cationized cellulose | 0.3 |
| (5) Chelating agent | Appropriate amount |
| (6) Preservative | Appropriate amount |
| (7) Perfume | Appropriate amount |
| (8) Purified water | Balance |

(Preparation Method)
Purified water was heated up to 70° C., the other ingredients were added to it and dissolved homogeneously, then it was cooled.

Example 7
Body Shampoo

| | wt % |
|---|---|
| (1) Sodium N-methyltaurate N-lauroylmethyltaurate | 3.0 |
| (2) Sodium N-methyltaurate laurate | 5.0 |
| (3) Lauric acid | 1.0 |
| (4) Myristic acid | 4.0 |
| (5) Palmitic acid | 2.0 |
| (6) Potassium hydroxide | 1.5 |
| (7) Coconut fatty acid monoethanol amide | 2.0 |
| (8) Glycerine | 5.0 |
| (9) Chelating agent | Appropriate amount |
| (10) Preservative | Appropriate amount |
| (11) Perfume | Appropriate amount |
| (12) Purified water | Balance |

(Preparation Method)
Purified water was heated up to 70° C., the other ingredients were added to it and dissolved homogeneously, then it was cooled.

All of Examples 1–7 have superior foaming properties, are free from sliminess after use, and have superior usability.

2. Examples of claims 11–20

(Test Samples 1 and 2, Control Samples 1–3)
Using the compounds shown in Table 12 (test samples 1 and 2 are, respectively, the compounds represented by the general formulas (1) and (2)), the foaming test and the actual use test were carried out for each sample. The results are shown in Table 13.

TABLE 12

| Sample No. | Compound name |
|---|---|
| Test sample 1 | Sodium hypotaurate N-lauroylmethyltaurate |
| Test sample 2 | Triethanol amine hypotaurate N-lauroylmethyltaurate |
| Control sample 1 | Sodium N-lauroylmethyltaurate |
| Control sample 2 | Potassium N-lauroylmethyltaurate |
| Control sample 3 | Triethanol amine N-lauroylmethyltaurate |

TABLE 13

| | Results of the foaming test | | Results of the actual use test | |
|---|---|---|---|---|
| | Foam height (cm) | Duration (min) | Foaming | Sliminess after use |
| Test sample 1 | 15.8 | 200 | ◉ | ○ |
| Test sample 2 | 16.0 | 150 | ◉ | ◉ |
| Control sample 1 | 11.5 | 40 | ◉ | x |
| Control sample 2 | 12.0 | 50 | ◉ | Δ |
| Control sample 3 | 13.0 | 70 | ◉ | x |

(Test Samples 3 and 4, Control Samples 4–6)

Using the compounds shown in Table 14 (test samples 3 and 4 are, respectively, the compounds represented by the general formulas (3) and (4)), the foaming test and the actual use test were carried out for each sample. The results are shown in Table 15.

TABLE 14

| Sample No. | Compound name |
|---|---|
| Test sample 3 | Sodium hypotaurate N-lauroyltaurate |
| Test sample 4 | Triethanol amine hypotaurate N-lauroyltaurate |
| Control sample 4 | Sodium N-lauroyltaurate |
| Control sample 5 | Potassium N-lauroyltaurate |
| Control sample 6 | Triethanol amine N-lauroyltaurate |

TABLE 15

| | Results of the foaming test | | Results of the actual use test | |
|---|---|---|---|---|
| | Foam height (cm) | Duration (min) | Foaming | Sliminess after use |
| Test sample 3 | 13.8 | 230 | ◉ | ◉ |
| Test sample 4 | 12.0 | 190 | ◉ | ◉ |
| Control sample 4 | 8.5 | 50 | ○ | Δ |
| Control sample 5 | 7.0 | 40 | ○ | Δ |

TABLE 15-continued

| | Results of the foaming test | | Results of the actual use test | |
|---|---|---|---|---|
| | Foam height (cm) | Duration (min) | Foaming | Sliminess after use |
| Control sample 6 | 8.0 | 95 | ○ | Δ |

(Test Samples 5 and 6, Control Samples 7–9)

Using the compounds shown in Table 16 (test samples 5 and 6 are, respectively, the compounds represented by the general formulas (5) and (6)), the foaming test and the actual use test were carried out for each sample. The results are shown in Table 17.

TABLE 16

| Sample No. | Compound name |
|---|---|
| Test sample 5 | Sodium hypotaurate laurylsulfuric ester |
| Test sample 6 | Triethanol amine hypotaurate laurylsulfuric ester |
| Control sample 7 | Sodium lauroylsulfuric ester |
| Control sample 8 | Potassium lauroylsulfuric ester |
| Control sample 9 | Triethanol amine lauroylsulfuric ester |

TABLE 17

| | Results of the foaming test | | Results of the actual use test | |
|---|---|---|---|---|
| | Foam height (cm) | Duration (min) | Foaming | Sliminess after use |
| Test sample 5 | 20.5 | 340 | ◉ | ◉ |
| Test sample 6 | 19.0 | 300 | ◉ | ○ |
| Control sample 7 | 18.0 | 100 | ◉ | x |
| Control sample 8 | 14.0 | 150 | ◉ | x |
| Control sample 9 | 13.9 | 90 | ◉ | x |

(Test Samples 7 and 8, Control Samples 10–12)

Using the compounds shown in Table 18 (test samples 7 and 8 are, respectively, the compounds represented by the general formulas (7) and (8)), the foaming test and the actual use test were carried out for each sample. The results are shown in Table 19.

TABLE 18

| Sample No. | Compound name |
|---|---|
| Test sample 7 | Sodium hypotaurate polyoxytethylenelauryl ether sulfuric ester |
| Test sample 8 | Triethanol amine hypotaurate polyoxytethylenelauryl ether sulfuric ester |
| Control sample 10 | Sodium polyoxytethylenelauryl ether sulfuric ester |
| Control sample 11 | Potassium polyoxytethylenelauryl ether sulfuric ester |
| Control sample 12 | Triethanol amine polyoxytethylenelauryl ether sulfuric ester |

TABLE 19

| | Results of the foaming test | | Results of the actual use test | |
|---|---|---|---|---|
| | Foam height (cm) | Duration (min) | Foaming | Sliminess after use |
| Test sample 7 | 16.5 | 250 | ◎ | ◎ |
| Test sample 8 | 15.0 | 300 | ◎ | ◎ |
| Control sample 10 | 10.0 | 80 | ◎ | x |
| Control sample 11 | 12.0 | 100 | ◎ | x |
| Control sample 12 | 9.8 | 75 | ○ | x |

(Test Samples 9 and 10, Control Samples 13–15)

Using the compounds shown in Table 20 (test samples 9 and 10 are, respectively, the compounds represented by the general formulas (9) and (10)), the foaming test and the actual use test were carried out for each sample. The results are shown in Table 21.

TABLE 20

| Sample No. | Compound name |
|---|---|
| Test sample 9 | Sodium hypotaurate laurylsulfonate |
| Test sample 10 | Triethanol amine hypotaurate laurylsulfonate |
| Control sample 13 | Sodium laurylsulfonate |
| Control sample 14 | Potassium laurylsulfonate |
| Control sample 15 | Triethanol amine laurylsulfonate |

TABLE 21

| | Results of the foaming test | | Results of the actual use test | |
|---|---|---|---|---|
| | Foam height (cm) | Duration (min) | Foaming | Sliminess after use |
| Test sample 9 | 22.5 | 470 | ◎ | ◎ |
| Test sample 10 | 19.0 | 390 | ◎ | ○ |
| Control sample 13 | 14.0 | 120 | ◎ | x |
| Control sample 14 | 13.5 | 95 | ◎ | x |
| Control sample 15 | 15.8 | 70 | ◎ | x |

The above results indicate that the test samples, compared with the control samples, have superior foaming and duration of foam and do not give rise to sliminess after use.

Specific examples of the detergent composition pertaining to the present invention are shown below. The blend ratios are expressed in weight percent units.

Example 1
Shampoo

| | wt % |
|---|---|
| (1) Ethylene glycol fatty acid ester | 2.0 |
| (2) Sodium hypotaurate N-lauroylmethyltaurate | 10.0 |
| (3) Dodecyl maltoside | 5.0 |
| (4) Laurylsulfobetaine | 10.0 |
| (5) Diethanolamide laurate | 5.0 |
| (6) Propylene glycol | 2.0 |
| (7) Coloring agent, perfume | Appropriate amount |
| (8) Purified water | Balance |

(Preparation Method)

Purified water was heated up to 70° C., the other ingredients were added to it and dissolved homogeneously, then it was cooled.

Example 2
Shampoo

| | wt % |
|---|---|
| (1) Sodium cocoylmethyl taurate | 8.0 |
| (2) Triethanolamine hypotaurate laurylsulfuric ester | 20.0 |
| (3) Diethanol amide of coconut fatty acid | 4.0 |
| (4) Perfume | Appropriate amount |
| (5) EDTA · 2Na | Appropriate amount |
| (6) Purified water | Balance |

(Preparation Method)

Purified water was heated up to 70° C., the other ingredients were added to it and dissolved homogeneously, then it was cooled.

Example 3
Body Shampoo

| | wt % |
|---|---|
| (1) Glycerine | 5.0 |
| (2) Potassium hypotaurate polyoxyethylenelauryl ether sulfuric ester | 5.0 |
| (3) Myristic ester of sucrose | 1.0 |
| (4) Triethanolamine laurate | 10.0 |
| (5) Sodium laurylsulfonsuccinate | 5.0 |
| (6) Diethanol amide of coconut oil | 3.0 |
| (7) Chelating agent | 0.1 |
| (8) Coloring agent, perfume | Appropriate amount |
| (9) Purified water | Balance |

(Preparation Method)

Purified water was heated up to 70° C., the other ingredients were added to it and dissolved homogeneously, then it was cooled.

Example 4
Liquid Soap

| | wt % |
|---|---|
| (1) Lauric acid | 3.0 |
| (2) Myristic acid | 7.0 |
| (3) Palmitic acid | 3.0 |
| (4) Oleic acid | 2.5 |
| (5) Lauroyldiethanolamide | 6.0 |

-continued

| | wt % |
|---|---|
| (6) Propylene glycol | 11.0 |
| (7) Erythritol | 4.0 |
| (8) Sodium hypotaurate N-lauroylmethyltaurate | 10.0 |
| (9) Sucrose | 5.0 |
| (10) Sodium hydroxide | 3.0 |
| (11) EDTA | 0.1 |
| (12) Perfume | Appropriate amount |
| (13) Purified water | Balance |

(Preparation Method)

Purified water was heated up to 70° C., the other ingredients were added to it and dissolved homogeneously, then it was cooled.

Example 5
Liquid Detergent for Clothes

| | wt % |
|---|---|
| (1) Sodium POE (3 moles) lauryl ether sulfate | 10.0 |
| (2) Maltotritol dodecyl ether | 30.0 |
| (3) Sodium N-lauroylhypotaurate | 15.0 |
| (4) Distearyldimethylammonium chloride | 2.0 |
| (5) Bleach | Appropriate amount |
| (6) Purified water | Balance |

(Preparation Method)

Purified water was heated up to 70° C., the other ingredients were added to it and dissolved homogeneously, then it was cooled.

All of Examples 1–5 have superior foaming properties, are free from sliminess after use, and have superior usability.

3. Examples of claims 21–30

(Test Samples 1 and 2, Control Samples 1–3)

Using the compounds shown in Table 22 (test samples 1 and 2 are, respectively, the compounds represented by the general formulas (1) and (2)), the foaming test and the actual use test were carried out for each sample. The results are shown in Table 23.

TABLE 22

| Sample No. | Compound name |
|---|---|
| Test sample 1 | Sodium taurate N-lauroylmethyltaurate |
| Test sample 2 | Triethanol amine taurate N-lauroylmethyltaurate |
| Control sample 1 | Sodium N-lauroylmethyltaurate |
| Control sample 2 | Potassium N-lauroylmethyltaurate |
| Control sample 3 | Triethanol amine N-lauroylmethyltaurate |

TABLE 23

| | Results of the foaming test | | Results of the actual use test | |
|---|---|---|---|---|
| | Foam height (cm) | Duration (min) | Foaming | Sliminess after use |
| Test sample 1 | 14.8 | 240 | ⊚ | ⊚ |
| Test sample 2 | 15.0 | 210 | ⊚ | ⊚ |

TABLE 23-continued

| | Results of the foaming test | | Results of the actual use test | |
|---|---|---|---|---|
| | Foam height (cm) | Duration (min) | Foaming | Sliminess after use |
| Control sample 1 | 9.5 | 100 | ○ | x |
| Control sample 2 | 11.0 | 65 | ⊚ | Δ |
| Control sample 3 | 11.8 | 70 | ○ | x |

(Test Samples 3 and 4, Control Samples 4–6)

Using the compounds shown in Table 24 (test samples 3 and 4 are, respectively, the compounds represented by the general formulas (3) and (4)), the foaming test and the actual use test were carried out for each sample. The results are shown in Table 25.

TABLE 24

| Sample No. | Compound name |
|---|---|
| Test sample 3 | Sodium taurate N-lauroyltaurate |
| Test sample 4 | Triethanol amine taurate N-lauroyltaurate |
| Control sample 4 | Sodium N-lauroyltaurate |
| Control sample 5 | Potassium N-lauroyltaurate |
| Control sample 6 | Triethanol amine N-lauroyltaurate |

TABLE 25

| | Results of the foaming test | | Results of the actual use test | |
|---|---|---|---|---|
| | Foam height (cm) | Duration (min) | Foaming | Sliminess after use |
| Test sample 3 | 14.5 | 300 | ⊚ | ⊚ |
| Test sample 4 | 12.0 | 210 | ⊚ | ⊚ |
| Control sample 4 | 11.5 | 100 | ⊚ | Δ |
| Control sample 5 | 9.0 | 85 | ○ | Δ |
| Control sample 6 | 8.0 | 90 | ○ | Δ |

(Test Samples 5 and 6, Control Samples 7–9)

Using the compounds shown in Table 26 (test samples 5 and 6 are, respectively, the compounds represented by the general formulas (5) and (6)), the foaming test and the actual use test were carried out for each sample. The results are shown in Table 27.

TABLE 26

| Sample No. | Compound name |
|---|---|
| Test sample 5 | Sodium taurate laurylsulfuric ester |
| Test sample 6 | Triethanol amine taurate laurylsulfuric ester |
| Control sample 7 | Sodium lauroylsulfuric ester |
| Control sample 8 | Potassium lauroylsulfuric ester |

TABLE 26-continued

| Sample No. | Compound name |
|---|---|
| Control sample 9 | Triethanol amine lauroylsulfuric ester |

TABLE 27

| | Results of the foaming test | | Results of the actual use test | |
|---|---|---|---|---|
| | Foam height (cm) | Duration (min) | Foaming | Sliminess after use |
| Test sample 5 | 21.5 | 300 | ◎ | ◎ |
| Test sample 6 | 23.0 | 330 | ◎ | ○ |
| Control sample 7 | 18.0 | 150 | ◎ | x |
| Control sample 8 | 19.5 | 100 | ◎ | x |
| Control sample 9 | 13.0 | 145 | ○ | Δ |

(Test Samples 7 and 8, Control Samples 10–12)

Using the compounds shown in Table 28 (test samples 7 and 8 are, respectively, the compounds represented by the general formulas (7) and (8)), the foaming test and the actual use test were carried out for each sample. The results are shown in Table 29.

TABLE 28

| Sample No. | Compound name |
|---|---|
| Test sample 7 | Sodium taurate polyoxytethylenelauryl ether sulfuric ester |
| Test sample 8 | Triethanol amine taurate polyoxytethylenelauryl ether sulfuric ester |
| Control sample 10 | Sodium polyoxytethylenelauryl ether sulfuric ester |
| Control sample 11 | Potassium polyoxytethylenelauryl ether sulfuric ester |
| Control sample 12 | Triethanol amine polyoxytethylenelauryl ether sulfuric ester |

TABLE 29

| | Results of the foaming test | | Results of the actual use test | |
|---|---|---|---|---|
| | Foam height (cm) | Duration (min) | Foaming | Sliminess after use |
| Test sample 7 | 15.5 | 220 | ◎ | ◎ |
| Test sample 8 | 17.0 | 285 | ◎ | ○ |
| Control sample 10 | 13.5 | 110 | ◎ | x |
| Control sample 11 | 12.0 | 100 | ◎ | x |
| Control sample 12 | 9.8 | 75 | ○ | x |

(Test Samples 9 and 10, Control Samples 13–15)

Using the compounds shown in Table 30 (test samples 9 and 10 are, respectively, the compounds represented by the general formulas (9) and (10)), the foaming test and the actual use test were carried out for each sample. The results are shown in Table 31.

TABLE 30

| Sample No. | Compound name |
|---|---|
| Test sample 9 | Sodium taurate laurylsulfonate |
| Test sample 10 | Triethanol amine taurate laurylsulfonate |
| Control sample 13 | Sodium laurylsulfonate |
| Control sample 14 | Potassium laurylsulfonate |
| Control sample 15 | Triethanol amine laurylsulfonate |

TABLE 31

| | Results of the foaming test | | Results of the actual use test | |
|---|---|---|---|---|
| | Foam height (cm) | Duration (min) | Foaming | Sliminess after use |
| Test sample 9 | 21.5 | 370 | ◎ | ◎ |
| Test sample 10 | 19.0 | 350 | ◎ | ○ |
| Control sample 13 | 14.5 | 80 | ◎ | x |
| Control sample 14 | 13.0 | 95 | ◎ | x |
| Control sample 15 | 15.0 | 60 | ◎ | x |

The above results indicate that the test samples, compared with the control samples, have superior foaming and duration of foam and do not give rise to sliminess after use.

Specific examples of the detergent composition pertaining to the present invention are shown below. The blend ratios are expressed in weight percent units.

Example 1

Shampoo

| | wt % |
|---|---|
| (1) Ethylene glycol fatty acid ester | 2.0 |
| (2) Sodium taurate N-lauroylmethyltaurate | 10.0 |
| (3) Dodecyl maltoside | 5.0 |
| (4) Laurylsulfobetaine | 10.0 |
| (5) Diethanolamide laurate | 5.0 |
| (6) Propylene glycol | 2.0 |
| (7) Coloring agent, perfume | Appropriate amount |
| (8) Purified water | Balance |

(Preparation Method)

Purified water was heated up to 70° C., the other ingredients were added to it and dissolved homogeneously, then it was cooled.

Example 2

Shampoo

| | wt % |
|---|---|
| (1) Sodium cocoylmethyl taurate | 8.0 |
| (2) Triethanolamine taurate laurylsulfuric ester | 20.0 |
| (3) Diethanol amide of coconut fatty acid | 4.0 |
| (4) Perfume | Appropriate amount |

-continued

| | wt % |
|---|---|
| (5) EDTA · 2Na | Appropriate amount |
| (6) Purified water | Balance |

(Preparation Method)

Purified water was heated up to 70° C., the other ingredients were added to it and dissolved homogeneously, then it was cooled.

Example 3

Body Shampoo

| | wt % |
|---|---|
| (1) Glycerine | 5.0 |
| (2) Potassium taurate polyoxyethylenelauryl ether sulfuric ester | 5.0 |
| (3) Myristic ester of sucrose | 1.0 |
| (4) Triethanolamine laurate | 10.0 |
| (5) Sodium laurylsulfonsuccinate | 5.0 |
| (6) Diethanol amide of coconut oil | 3.0 |
| (7) Chelating agent | 0.1 |
| (8) Coloring agent, perfume | Appropriate amount |
| (9) Purified water | Balance |

(Preparation Method)

Purified water was heated up to 70° C., the other ingredients were added to it and dissolved homogeneously, then it was cooled.

Example 4

Liquid Soap

| | wt % |
|---|---|
| (1) Lauric acid | 3.0 |
| (2) Myristic acid | 7.0 |
| (3) Palmitic acid | 3.0 |
| (4) Oleic acid | 2.5 |
| (5) Lauroyldiethanolamide | 6.0 |
| (6) Propylene glycol | 11.0 |
| (7) Erythritol | 4.0 |
| (8) Sodium taurate N-lauroylmethyltaurate | 10.0 |
| (9) Sucrose | 5.0 |
| (10) Sodium hydroxide | 3.0 |
| (11) EDTA | 0.1 |
| (12) Perfume | Appropriate amount |
| (13) Purified water | Balance |

(Preparation Method)

Purified water was heated up to 70° C., the other ingredients were added to it and dissolved homogeneously, then it was cooled.

Example 5

Liquid Detergent for Clothes

| | wt % |
|---|---|
| (1) Sodium POE (3 moles) lauryl ether sulfate | 10.0 |
| (2) Maltotritol dodecyl ether | 30.0 |
| (3) Sodium N-lauroyltaurate | 15.0 |
| (4) Distearyldimethylammonium chloride | 2.0 |
| (5) Bleach | Appropriate amount |
| (6) Purified water | Balance |

(Preparation Method)

Purified water was heated up to 70° C., the other ingredients were added to it and dissolved homogeneously, then it was cooled.

All of Examples 1–5 have superior foaming properties, are free from sliminess after use, and have superior usability.

What is claimed is:

1. A detergent composition which contains as an essential ingredient an alkali metal N-methyltaurate salt of a N-acylmethyltaurine represented by the following general formula 1-(1).

$$R-CO-N(CH_3)-CH_2-CH_2-SO_3^-H_2N^+(CH_3)-CH_2-CH_2-SO_3^-X^+ \quad \text{1-(1)}$$

(In this formula, R denotes a saturated or unsaturated hydrocarbon group with a carbon number of 7–23 and X denotes an alkali metal).

2. A detergent composition which contains as an essential ingredient an organic alkali N-methyltaurate salt of a N-acylmethyltaurine represented by the following general formula 1-(2).

$$R-CO-N(CH_3)-CH_2-CH_2-SO_3^-H_2N^+(CH_3)-CH_2-CH_2-SO_3^-Y^+ \quad \text{1-(2)}$$

(In this formula, R denotes a saturated or unsaturated hydrocarbon group with a carbon number of 7–23 and Y denotes an organic alkali).

3. A detergent composition which contains as an essential ingredient an alkali metal N-methyltaurate salt of a N-acyltaurine represented by the following general formula 1-(3).

$$R-CO-NH-CH_2-CH_2-SO_3^-H_2N^+(CH_3)-CH_2-CH_2-SO_3^-X^+ \quad \text{1-(3)}$$

(In this formula, R denotes a saturated or unsaturated hydrocarbon group with a carbon number of 7–23, and X denotes an alkali metal).

4. A detergent composition which contains as an essential ingredient an organic alkali N-methyltaurate salt of a N-acyltaurine represented by the following general formula 1-(4).

$$R-CO-NH-CH_2-CH_2-SO_3^-H_2N^+(CH_3)-CH_2-CH_2-SO_3^-Y^+ \quad \text{1-(4)}$$

(In this formula, R denotes a saturated or unsaturated hydrocarbon group with a carbon number of 7–23 and Y denotes an organic alkali).

* * * * *